US012575942B2

(12) United States Patent
Caratsch

(10) Patent No.: US 12,575,942 B2
(45) Date of Patent: Mar. 17, 2026

(54) FLEXIBLE INTERBODY CAGE

(71) Applicant: Alexander Caratsch, Trelex (CH)

(72) Inventor: Alexander Caratsch, Trelex (CH)

(73) Assignee: Alexander Caratsch, Trelex (CH)

( * ) Notice: Subject to any disclaimer, the term of this patent is extended or adjusted under 35 U.S.C. 154(b) by 0 days.

(21) Appl. No.: 18/864,566

(22) PCT Filed: May 11, 2023

(86) PCT No.: PCT/CH2023/050014
§ 371 (c)(1),
(2) Date: Nov. 11, 2024

(87) PCT Pub. No.: WO2023/216003
PCT Pub. Date: Nov. 16, 2023

(65) Prior Publication Data
US 2025/0312170 A1 Oct. 9, 2025

(30) Foreign Application Priority Data

| | | |
|---|---|---|
| May 13, 2022 | (CH) | CH00586/2022 |
| Oct. 2, 2022 | (CH) | CH1183/2022 |
| Nov. 3, 2022 | (CH) | CH1301/2022 |
| Nov. 8, 2022 | (CH) | CH1339/2022 |

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/3006* (2013.01); *A61F 2002/30579* (2013.01); *A61F 2002/30604* (2013.01); *A61F 2002/3092* (2013.01); *A61F 2002/3093* (2013.01)

(58) Field of Classification Search
CPC ...................................................... A61F 2/447
See application file for complete search history.

(56) References Cited

U.S. PATENT DOCUMENTS

2006/0287725 A1* 12/2006 Miller ................... A61F 2/4455
623/17.11
2010/0137989 A1 6/2010 Armstrong et al.
(Continued)

FOREIGN PATENT DOCUMENTS

EP 2910219 A1 8/2015
WO WO2005/092250 A1 10/2005
(Continued)

OTHER PUBLICATIONS

International Search Report dated Sep. 7, 2023, for PCT Application No. PCT/CH2023/050014, filed on May 11, 2023, 4 pages.
(Continued)

*Primary Examiner* — Andrew Yang
(74) *Attorney, Agent, or Firm* — Girma Wolde-Michael

(57) ABSTRACT
An intervertebral bone fusion implantable device configured with flexible structural elements on its top and bottom surfaces for controlled dampening of the compressive force exerted on the device by two vertebrae and for the maximization of the contact surface between the device and the uneven endplates of the vertebrae.

7 Claims, 10 Drawing Sheets

(56)                    References Cited

U.S. PATENT DOCUMENTS

| | | | |
|---|---|---|---|
| 2012/0150300 A1 | 6/2012 | Nihalani | |
| 2016/0354211 A1* | 12/2016 | Packer | .................. A61F 2/4611 |
| 2017/0209284 A1* | 7/2017 | Overes | .................. A61F 2/4611 |
| 2020/0093603 A1 | 3/2020 | Manwill et al. | |

FOREIGN PATENT DOCUMENTS

| | | |
|---|---|---|
| WO | WO2006/134262 A1 | 12/2006 |
| WO | WO2007/079021 A2 | 7/2007 |
| WO | WO2018/078148 A1 | 5/2018 |
| WO | WO2019/173130 A1 | 9/2019 |
| WO | WO2020/163278 A1 | 8/2020 |

OTHER PUBLICATIONS

Written Opinion of the International Searching Authority dated Sep. 7, 2023, for PCT Application No. PCT/CH2023/050014, filed on May 11, 2023, 9 pages.

* cited by examiner

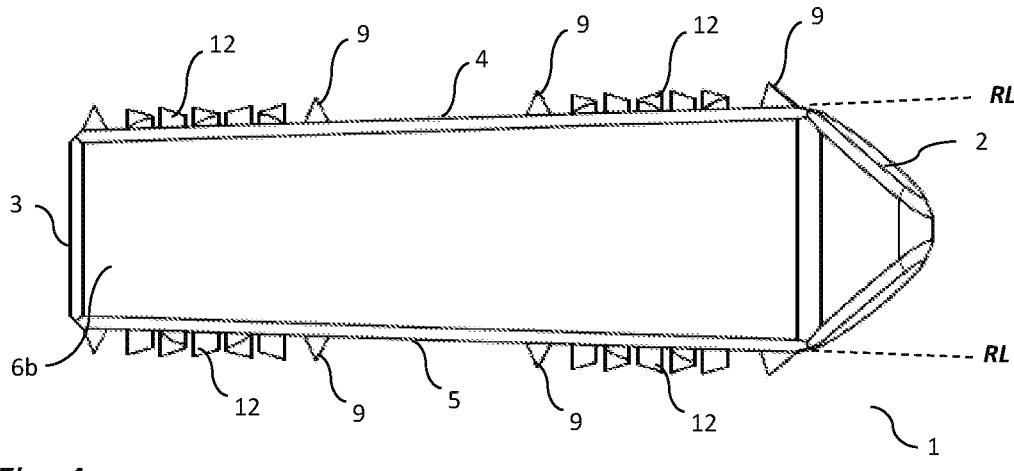
*Fig. 4*
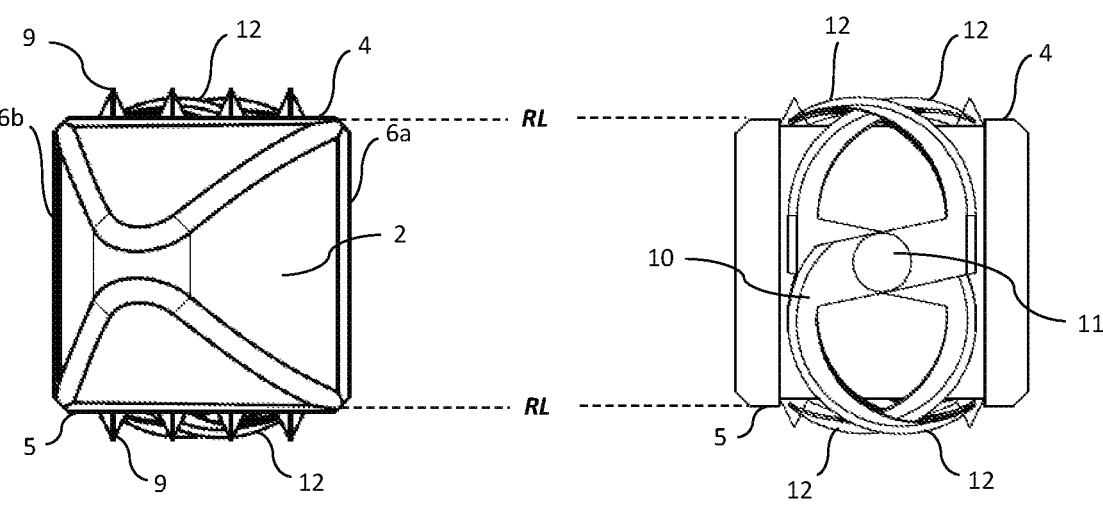
*Fig. 5*
*Fig. 6*

12
13
6b
13
14
2
_Fig. 7_
1
2
4
13
12
8
13
12
12
1
3
_Fig. 8_
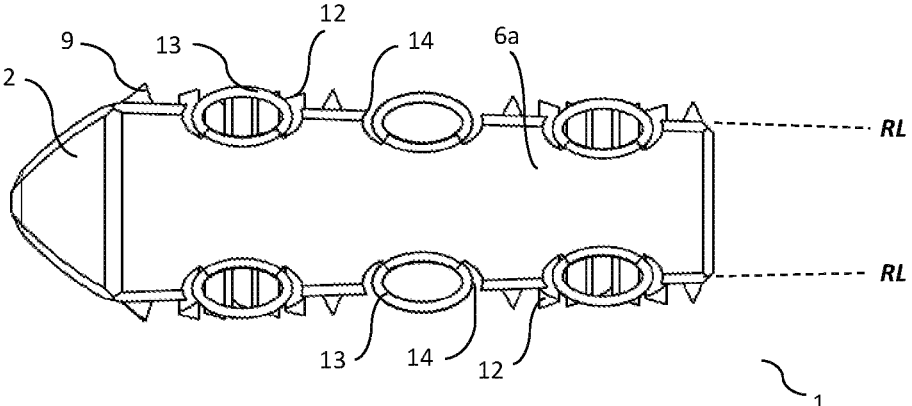
9     13     12     14     6a
2
RL
RL
13     14     12
1
_Fig. 9_

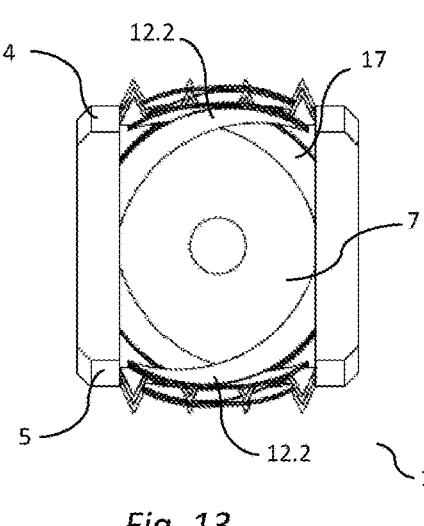
_Fig. 13_
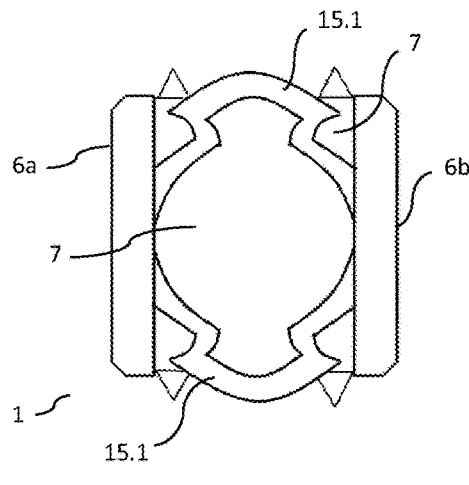
_Fig. 14_
_Fig. 15_
_Fig. 16_

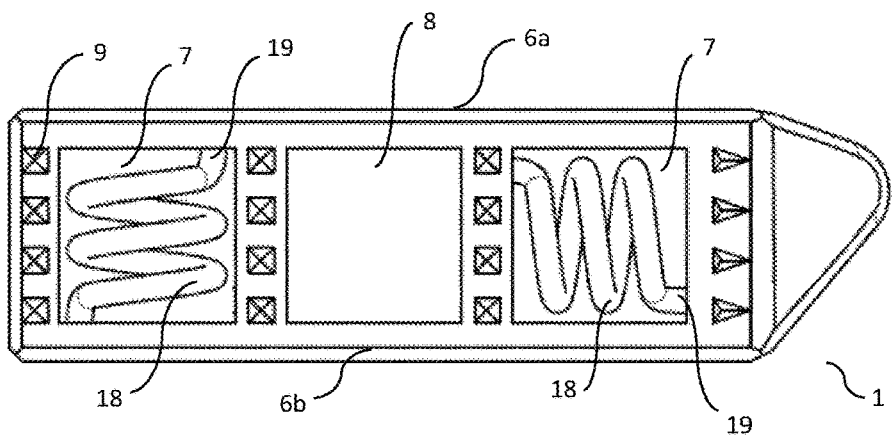
*Fig. 17*
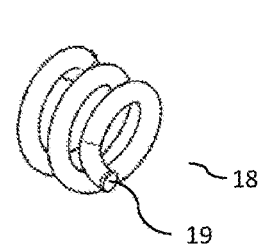
*Fig. 18*
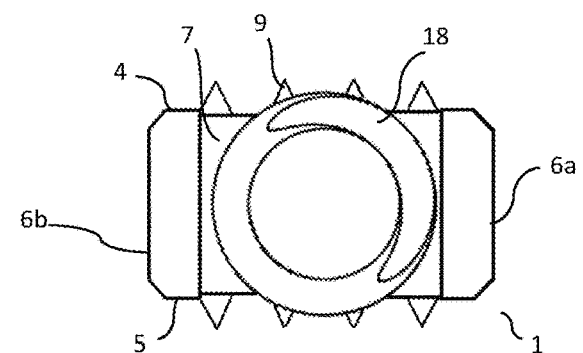
*Fig. 19*
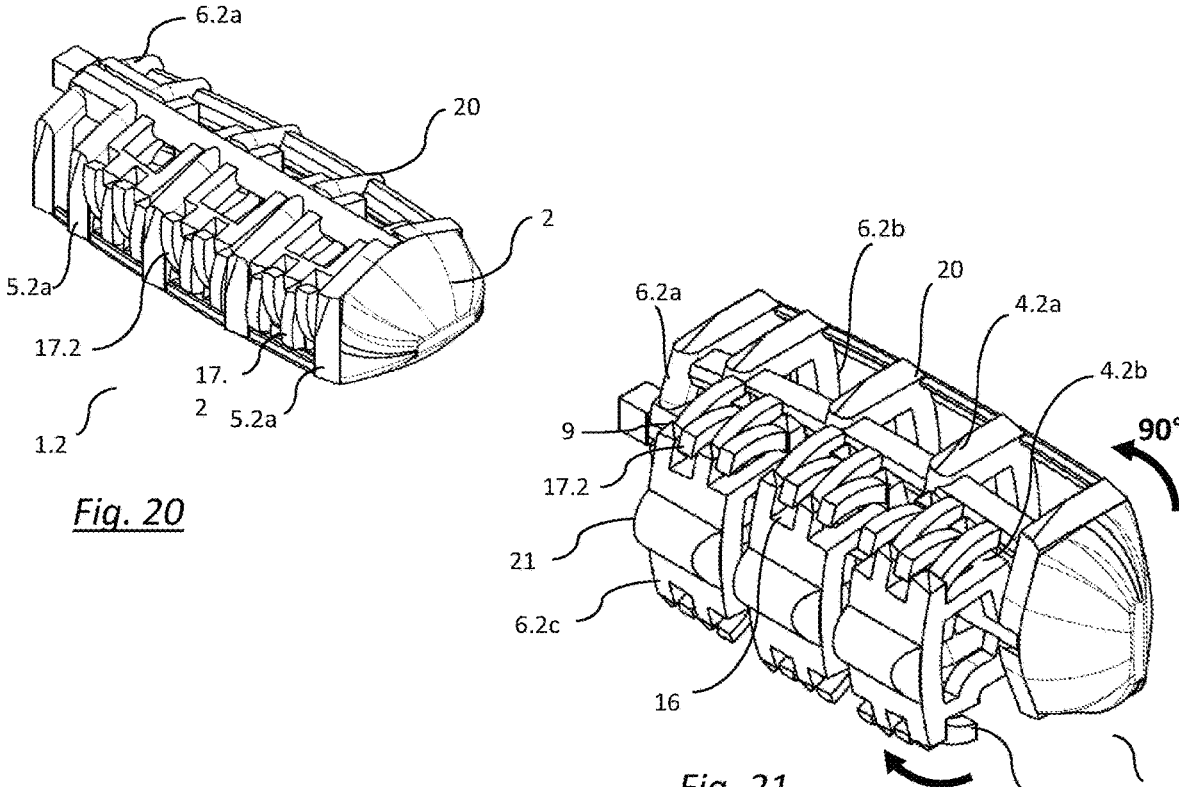
*Fig. 20*
*Fig. 21*

§

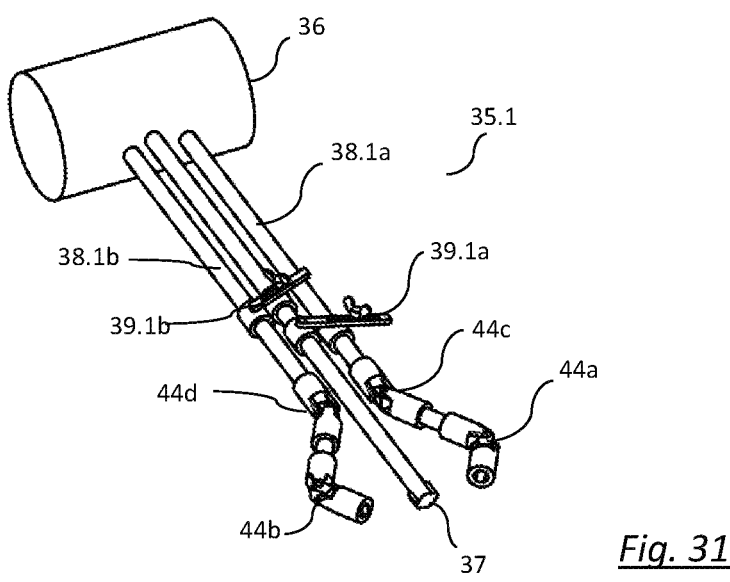
*Fig. 31*
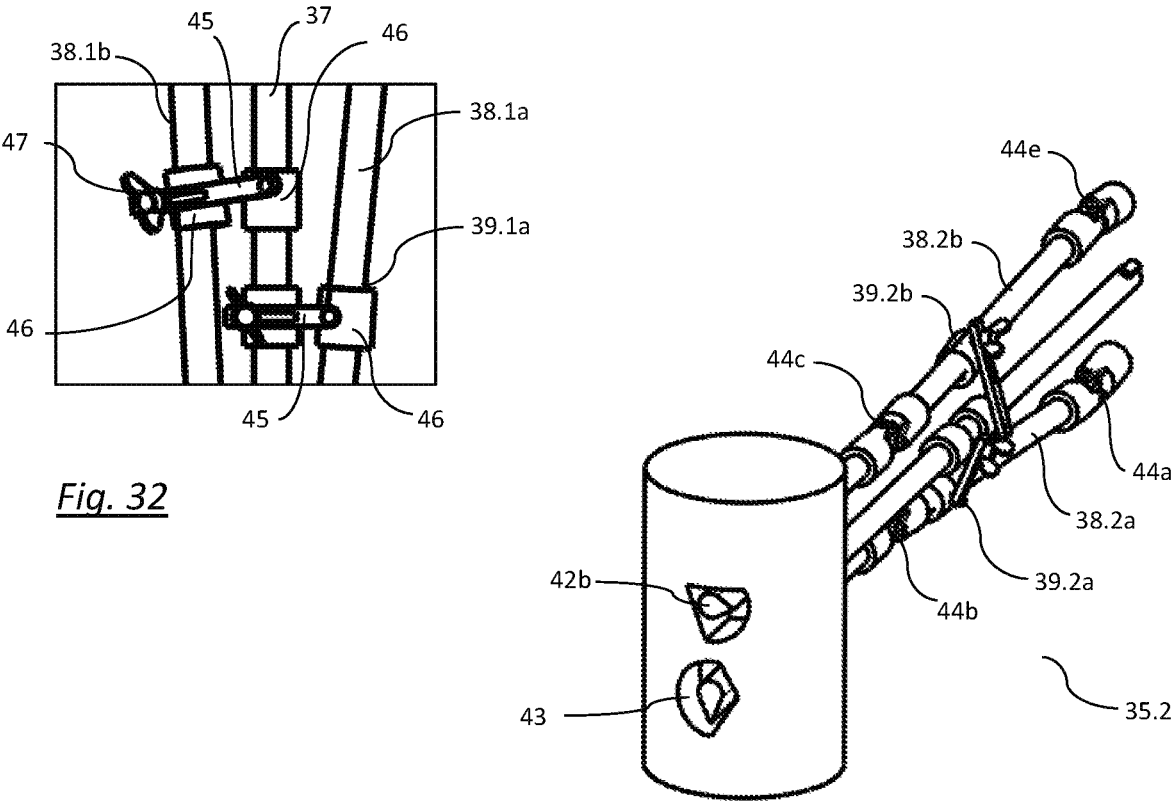
*Fig. 32*
*Fig. 33*

FLEXIBLE INTERBODY CAGE

The present invention relates to the medical field, and more particularly to a intervertebral implant with structurally restrained flexible top and bottom surfaces.

Certain pathologies of the spinal column, such as degenerated discs, facet diseases, and dislocation of vertebrae, compromise the support capacity of the column and the sharing of the load.

The treatment of such pathologies in their advanced stages is achieved by various stabilization systems with intra-discal implants such as interbody cages, which are typically coupled with extra-discal systems, which combine the use of vertebral screws and plates or rods to rigidly connect the two adjoining vertebrae. Such intra-discal implants have significantly improved the treatment of pathologies of the spinal column, by restoring the intervertebral space, which results in the decompression of the nerve roots and the acceleration of bony fusion of the adjoining vertebrae.

Impactation cages represent an important category among interbody cages. These cages, which have a substantially parallelepiped shape, are inserted between the vertebrae by impactation. Given the uneven anatomy of the vertebral endplates, cages made in a rigid material do not ensure homogenous load-sharing between the implant's surfaces and the endplates, which may cause the vertebrae to collapse around the implant—a phenomenon commonly known as "subsidence".

In order to overcome these challenges, interbody cages have been developed made of more flexible materials or dampening structures. WO2022/061477 discloses cages structured with thin plates configured to rest perpendicularly against vertebral endplates and arranged with slits and/or slots allowing for a buffer distance to narrow down the distance between the vertebrae when compression force is exercised on the cage. This disclosure also describes a cage configured with a rigid base and a flexible structure made of bundled strands fixed on the rigid base and arranged perpendicularly to the vertebral endplates. WO2022/23957 discloses intervertebral cages featuring dampening and/or flexible structures configured with split rings.

The purpose of the present invention is to provide an interbody cage comprising one or more flexible structures, suitable for dampening the compression force of the vertebral endplates on the interbody cage in a controlled way and for filling depressed surfaces on the vertebral endplates. The flexible structures of the preferred embodiment consist of thin "S"-shaped or "Z"-shaped springs, flexible strands or hoops, or coiled springs arranged in open chambers hollowed out in the cage or positioned within buffer openings arranged on the inner or outer walls of the interbody cage and/or on its top and bottom surfaces. The flexible structure may also be provided by convex mesh-structures arranged on the top and bottom surfaces of the interbody cage. The compression force exercised by the adjoining vertebrae are flexing the springs, strands, hoops, coils or convex mesh structures until the rigid borders of the chambers or lateral walls of the cage engage the vertebrae. Such walls and cage surfaces provide a rigid frame which stops any excess compression of the springs, strands, hoops coils and convex mesh structures below the peripheral level of the rigid frame. The hollowed-out rigid frame with its restraining feature, enables an effective control of the flexibility of the top and bottom surfaces of the interbody cage. Where the vertebral endplates present depressed portions on their surfaces, the springs, strands, hoops, coils or convex mesh structures still fill those depressed cavities, although their flexion is more limited.

In another embodiment of the invention, the flexibility of the cage is provided by top and bottom surfaces of the implant made in thin lattice or thin coiled structures. The rigid restraining frame feature of the invention may be provided by denser lattice or thicker coil structures, or homogenous rigid material, arranged below the flexible surface structures, or by the partial or full coating with denser or rigid material of the thin lattice or coiled structures on some of their inner and/or outer walls or sides. The flexibility of the surfaces of the cage are thus restrained by the denser or rigid material either present at a deeper level of the implant or coated on the sides of the thin lattice or coiled structures. The coating of the walls and sides of the mobile components of implants which are made of lattice or coiled structures also reduces the impact of friction generated by relative motions between several components of implants made with such structures, for example during pivoting motions.

An instrument to deliver the flexible cage of the invention is also disclosed. The cages of the first embodiment may be delivered by classic instruments known in the art, such as an instrument comprising a rod mounted with a handle at its proximal end and configured with a threaded distal end to engage a bore in the rear part of the intervertebral cage for the straightforward insertion by impactation of the cage. A more complex instrument may be used for the delivery and deployment of the flexible expandable cages of the invention, with one rod engaging the rear part of the hosting structure of the expandable cage for the insertion of the expandable cage between two vertebrae and the pivoting of the cage's hosting structure, and at least one mobile rod engaging the rear part of the cage's extension member, for pivoting the extension member for its deployment. This mobile rod may be configured with joints to enable the adjustment of the relative distance and positioning of the fixed and mobile rods to match the distance and align to the axis between the bore of the hosting structure of the cage and the fastening component of its pivoting extension member, regardless of the width of different sized cages.

The embodiments of the invention may apply to any implant constructs separating bones and/or for the fusion of any bones of a human or animal skeleton.

The characteristics of the invention will appear more clearly from the description of various embodiments and their variations, which are solely provided as examples and are not limitative, and in which references will notably be made to the anterior end or frontal or front end of the cage, thus defining that part of the cage which is adjusted against the vertebrae just before the introduction of said cage into the interbody space, and to the posterior end or rear-end of the cage, which shall define the part of the cage opposite the anterior end or front end. The words "pivoted" and "rotated" are used within the same meaning, to describe a motion around an axis. The description of these various embodiments refers to the attached schematic Figures in which:

FIG. 4 represents a lateral view of the cage in FIGS. 1 and 2.

FIG. 5 represents a front view of the cage in FIGS. 1,2 and 4.

FIG. 6 represents a cross-section of the cage in FIG. 5.

FIG. 7 represents a perspective front view of the cage with flexible oval hoops of the first variation of the first embodiment.

FIG. 8 represents a top view of the cage in FIG. 7.

FIG. 9 represents a lateral view of the cage in FIGS. 7 and 8.

FIG. 13 represents a cross-section of the cage of the third variation of the first embodiment with flexible strands mounted in inner chambers.

FIG. 14 represents a cross-section of the cage of the fourth variation of the first embodiment with flexible hoops mounted in inner chambers.

FIG. 15 represents a perspective rear view of the cage of the fifth variation of the first embodiment for an anterior surgical approach, with "Z"-shaped flexible overhanging members and flexible strands.

FIG. 16 represents a cross-section of the cage in FIG. 15.

FIG. 17 represents a top view of the cage of the sixth variation of the first embodiment with flexible coiled springs.

FIG. 18 represents a perspective view of the coiled spring of the cage in FIG. 17.

FIG. 19 represents a cross-section of the cage in FIG. 17.

FIG. 20 represents a perspective front view of the expandable cage of the second embodiment with flexible strands in stowed configuration.

FIG. 21 represents a perspective front view of the same expandable cage as in FIG. 20, in deployed configuration.

FIG. 31 represents a perspective view of a variation of the instrument with articulated rods.

FIG. 32 represents a detail of the modular connecting members between the rods of the instrument.

FIG. 33 represents a perspective view of the second variation of the instrument with articulated rods.

Figures 1, 2, 3:
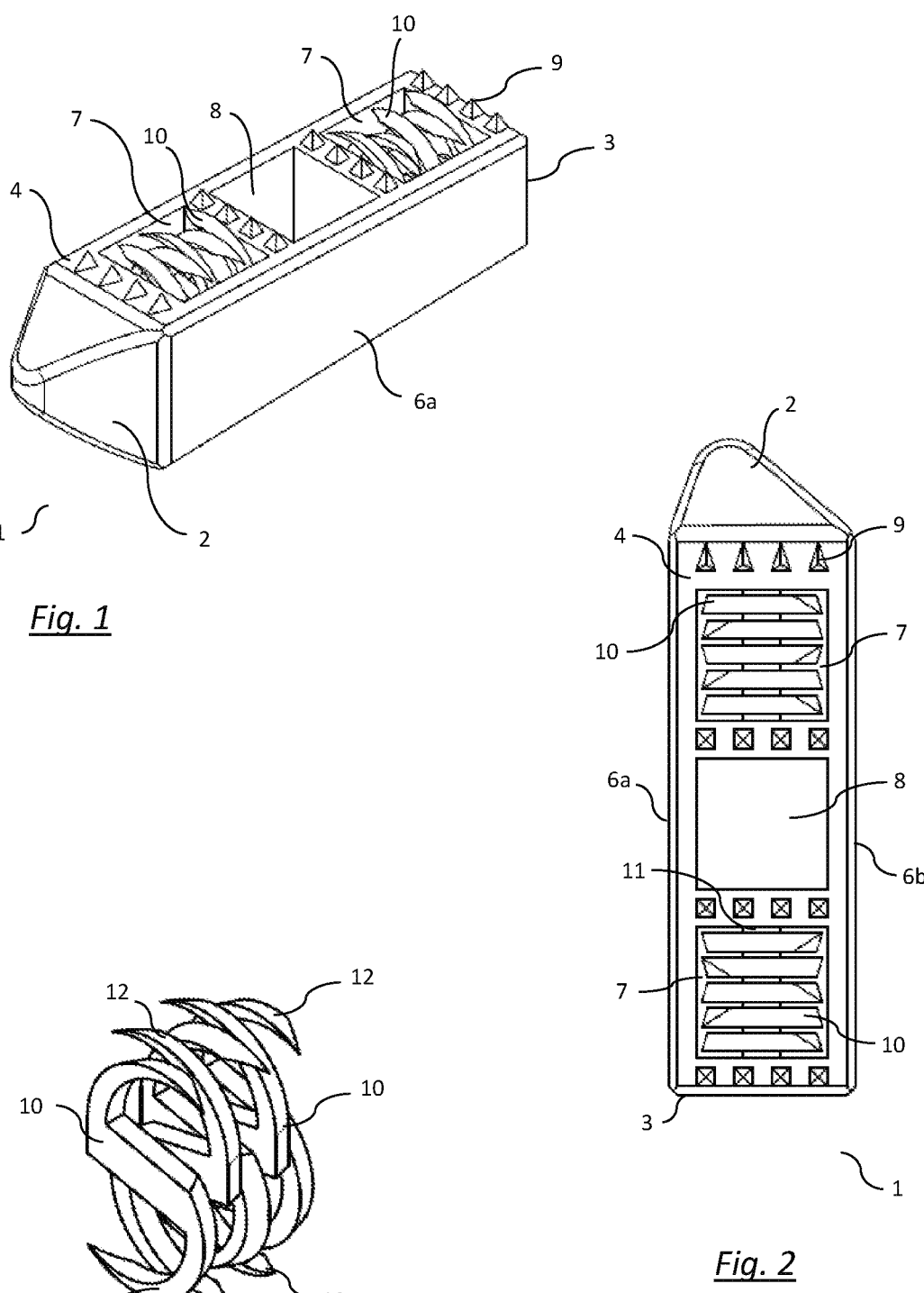
FIG. 1 represents a perspective front view of the cage with flexible "S"-shaped members of the first embodiment.
FIG. 2 represents a top view of the cage in FIG. 1.
FIG. 3 represents a perspective view of an assembly of "S"-shaped flexible members.

According to FIGS. 1 and 2, the first embodiment of the invention describes an interbody cage 1, for delivery via a posterior or transforaminal surgical approach between two vertebrae V1, V2 to maintain a separation space between the two vertebrae to achieve the fusion of the vertebral segment. The cage 1 has a front end 2 configured in the shape of a wedge for engaging the vertebrae V1, V2 for the insertion of the cage 1 and separation of the interbody space and a flat rear end 3, configured with a bore 40 for the fixation of the cage 1 to the rod 37 of a removable instrument 35 for the delivery of the cage 1. The cage 1 is arranged with planar top and bottom surfaces 4, 5 on which protruding anchoring means 9 are arranged to prevent the migration of the cage 1 within the interbody space. Two open chambers 7 are arranged between the top and bottom surfaces 4, 5 for the positioning of flexible members 10 therein, and one cavity 8 is arranged between the top and bottom surfaces 4, 5 for the stuffing of graft material. The cage 1 is also arranged with planar lateral surfaces 6a, 6b of the cage 1.

As shown in FIG. 3, the flexible members 10 positioned in the chambers 7 are thin individual members in the shape «S» arranged parallel to each other in opposite directions. The flexible members 10 may be attached to a median shaft 11 as represented in FIG. 2 et 6 or on any other type of structure connected to the inner walls of the chambers 7 of the cage 1. Each flexible member 10 is allowed to flex individually, so that the pressure of the vertebrae V1, V2 on the construct of parallelly aligned flexible members 10 shown in FIG. 3 is modulated by the magnitude of the force and the direction from which the compressive force is exerted on the individual flexible members 10. The individual flexible members 10 may have different stiffnesses relative to each other to further modulate the sharing of the load of the vertebrae V1, V2 on the cage 1.

According to FIGS. 4 to 6, the dimension between the extremities 12 of the "S"-shaped flexible members 10, in their extended configuration, is superior to the distance between the top and bottom surfaces 4, 5 of the cage 1 at the location of the chambers 7, so that the upper and lower ends 12 of the flexible "S"-shaped members 10 protrude beyond the top and bottom surfaces 4, 5 of the cage 1, and reach the height of the extremity of the anchoring means 9 arranged on the top and bottom surfaces 4, 5 of the cage 1. As shown in FIG. 6, in the extended configuration of the flexible members 10, the dimension of the width of the "S"-shaped flexible members 10 is smaller than the dimension of the width defined by the lateral inner walls of the chamber 7. The cage 1 is also configured so that in their flexed configuration the width of the flexible members 10 is smaller than the dimension between the inner walls of the chamber 7.

Once the cage has been delivered in the interbody space and compression force from the adjoining vertebrae V1, V2 of the segment resting on the cage 1 is applied against the upper and lower extremities 12 of the flexible members 10 of the cage 1, such upper and lower extremities 12 are allowed to flex within a space ranging down to the rigid levels "RL" defined by the rigid frames of the top and bottom surfaces 4, 5 of the cage and of the walls of the chambers 7. This is the flexed configuration of the flexible members 10.

In the flexed configuration of the extremities 12 of the flexible members 10, the first advantage is the durable dampening effect on the pressure otherwise exerted by the cage's top and bottom surfaces 4, 5 on the vertebral endplates during micro-motions of the vertebrae V1, V2, until fusion of the vertebral segment is achieved: this dampening effect enables a load-sharing of the uneven vertebral endplates V1, V2 on a broader surface of the cage 1 and protects the cancellous bone structure of the endplates of the verte-brae V1, V2 against subsidence. Secondly, this larger contact surface of the flexible members 10 with the endplates also creates a pressure-tension process on the bone structure, thus enhancing bone growth according to Wolff's Law. The slight cavities which are naturally present on the uneven endplates are filled by the non-flexed extremities 12 of the flexible members 10, individually or in groups of adjacent flexible members 10 (as shown in FIG. 3), and also ensure a small pressure between the depressed bone surfaces of the end-plates and the implant, thus furthering bone growth and improving the bone fusion process. Thirdly, the dampening effect of the flexible members 10 is controlled by the RL levels avoiding excessive pressure on the otherwise fragile structure of the flexible members 10. Fourthly, the flexibility of the flexible members 10 does not prevent the anchoring means on the top and bottom surfaces 4, 5 of the cage 1 to engage into the vertebral endplates to secure the cage 1 against migration. The fifth advantage of the invention, as shown in FIG. 4, is that the upper and lower extremities 12 of the flexible members 10 are arranged with bevelled cross-sections, which gives anchoring properties to these flexed extremities 12, in further support to the rigid anchor-ing means 9 against migration. Lastly, given the parallel positioning of the "S"-shaped flexible members 12 and the absence of any contact between their lateral extremities and the inner walls of the chambers 7, any flexion of the extremities 12 is friction-less, which prevents the wearing of the flexible members 10 and the creation of any debris.

A first variation of the cage 1 of the first embodiment is described in FIGS. 7 to 9, where the external walls 6a, 6b of the cage 1 are arranged on each side of the graft cavity 8, adjacent to the top and bottom surfaces 4, 5 of the cage 1, with an oval buffer aperture 14. A flexible member 10 in the shape of an oval hoop 13 is fixed to the bottom of each of the oval buffer apertures 14. The advantage of these oval hoops 13 is to provide flexibility to the cage 1 also at the level of its lateral walls 6a, 6b. When pressured by the vertebrae V1, V2, the oval hoops 13 are squeezed to a shorter dimension in their height, which in turn may extend their width without contact with the walls of the oval buffer apertures 14. The flexion of the oval hoops 13 within the oval buffer apertures 14 may thus be frictionless and remains restricted by the rigid level "RL" of the side walls of the graft cavity 8 and of the chambers 7, thus protecting the oval hoops 13 against excessive flexion and breakage.

Figure 10:
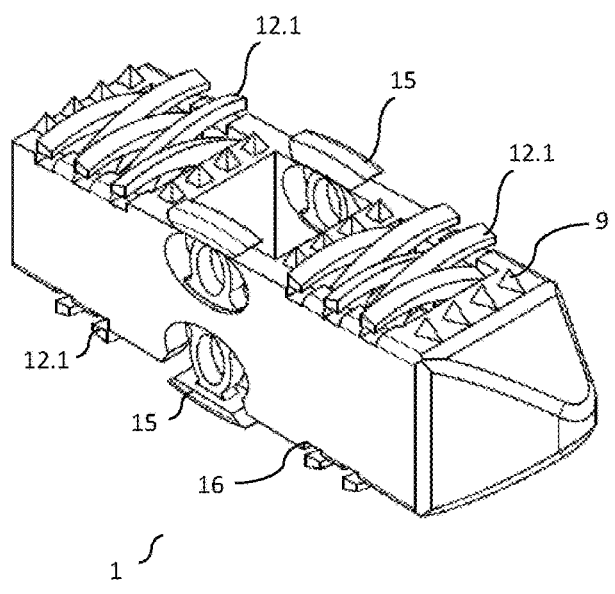
FIG. 10 represents a perspective front view of the cage with "Z"-shaped flexible overhanging members and capped hoops of the second variation of the first embodiment.
Figure 11:
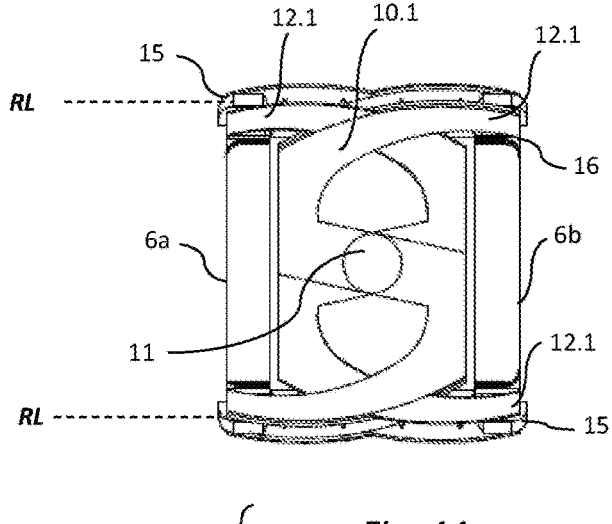
FIG. 11 represents a cross-section from a rear view of the cage in FIG. 10.
Figure 12:
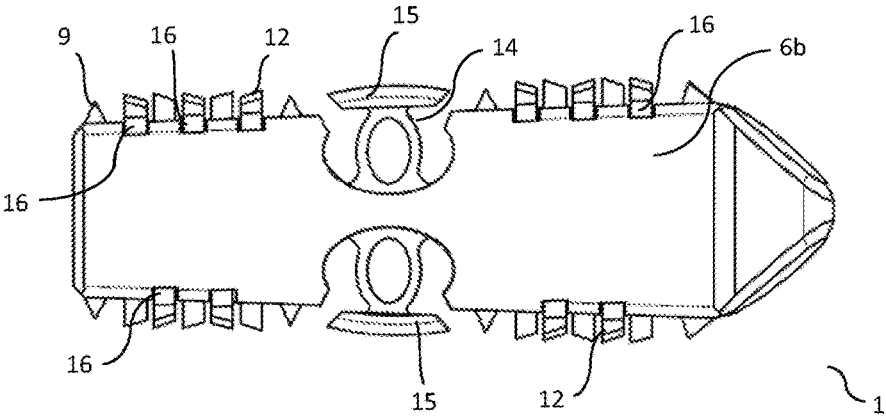
FIG. 12 represents a lateral view of the cage in FIG. 10.

FIGS. 10 to 12 describe a second variation of the first embodiment, where the cage 1 has flexible members 10.1 in the shape of a «Z», the extremities 12.1 of which are arranged to protrude beyond the top and bottom surfaces 4, 5 of the cage 1 and to overhang over the lateral walls 6a, 6b of the cage within buffer slits 16 cut into the top and bottom ends of such lateral walls 6a, 6b at the level of the chambers 7. The depth and width of the buffer slits 16 have larger dimensions than the height and thickness of the overhanging extremities 12.1 of the flexible members 10.1: under the compression force from the vertebrae V1, V2, the extremi-ties 12.1 of the «Z» shaped flexible members 10.1 are flexing into the buffer slits 16 while the portions of the lateral walls 6a, 6b which are not arranged with slits 14 serve as rigid frame defining the rigid level "RL" to restrain any over-flexion of the flexible members 10.1 and thus prevent any contact or friction of their overhanging extremities 12.1 with the bottoms or inner walls of the buffer slits 16. This second variation of the first embodiment also extends the controlled flexible structure of the cage 1 to the lateral walls 6a, 6b at the level of the chambers 7. As shown in FIGS. 10 and 12, in this variation, the oval hoop structure 14 of the previous variation is replaced by a hoop structure 15 mounted with an arched cap allowing for motions within the oval buffer apertures 14.

FIGS. 13 and 14 describe further variations of the first embodiment of the invention: as shown in FIG. 13, the cage 1 of this third variation is arranged with flexible parallel strands 17 configured, in their length, in planes generally similar to the planes of the adjacent endplates of the verte-brae V1, V2, each strand 17 being individually fixed to one of the inner walls of the chambers 7 of the cage 1. The dimension of these strands 17 in their length is smaller than the dimension of the width of the chamber 7, and these strands 17 being unrestrained at their extremity 12.2, they ensure the flexible feature of the invention, while the rigid frame of the chamber 7 serves as restraining element defin-ing the rigid level "RL" according to the principle of the invention. The chamber 7 may also be packed with graft material which may be loaded via an aperture made in the lateral walls 6a, 6b of the cage 1; the graft material promotes bone growth between the strands 17 to connect with the bone structure of the endplates. A fourth variation is shown in FIG. 14, where the flexing member is provided by hoops 15.1 mounted on two inner walls of the chambers 7, pro-truding from above the top and bottom surfaces 4, 5 of the cage 1, defining the rigid levels "RL". These hoops 15.1 are structured with sections which are arched in opposite direc-tions to offer variable directional flexibility to the hoop 15.1.

The cages 1 of the first to fourth variation of the first embodiment may be inserted between the upper and lower vertebrae V1, V2 oriented with their lateral surfaces 6a, 6b engaging the vertebrae, and once the cage 1 is in its final location, it is rotated 90° in order for the top and bottom surfaces 4, 5 of the cage 1 with the protruding flexible members 10, hoops 13, 15 or strands 17, to engage the vertebrae V1, V2 for the fusion process.

A fifth variation of the first embodiment is described in FIGS. 15 and 16, with a cage 1.1 designed for an anterior surgical approach, arranged with a combination of different flexible structures. «Z»-shaped flexible members 10.1 are mounted within two lateral chambers 7.1 and have over-hanging extremities 12.1 positioned within buffer slits 16 cut into the lateral walls 6a, 6b of the cage 1.1. In addition, flexible strands 17.1 are positioned within buffer slits 16 cut in the top and bottom surfaces 4, 5 adjacent to the front and rear ends 2, 3 of the cage 1.1. The «Z»-shaped flexible members 10.1 and the flexible strands 17.1 may flex within the respective buffer slits 16, while the rigid top and bottom surfaces 4, 5 of the cage 1.1, which are also supporting the anchoring means 9, prevent their over-flexing and any friction with the bottom of the buffer slits 16. The cage 1.1 of this variation is maximizing the flexible surface of its top and bottom surfaces 4, 5.

FIG. 17 represents a sixth variation of the first embodi-ment of the invention, where each of the chambers 7 of the cage 1 is arranged with a coiled spring 18 (shown in FIG. 18) mounted, by its ends 19, to two inner walls of the chambers 7: one of the coiled springs 18 is mounted to two of the lateral walls 6a, 6b and the other coiled spring 18 is mounted to inner walls in the longitudinal axis of the cage 1. FIG. 19 shows that the height/width of the coiled springs 18 exceed the dimension between the top and bottom surfaces 4, 5 of the cage 1 and the coiled springs 18 plays the same role as the flexible members 10, 10.1 and strands 17 of the previous variations. In additional variations, coiled springs 18 may be mounted by one of its ends 19 only to one inner wall or to one of the upper or lower surfaces 4, 5 of the cage 1, or through the side of one or more of its hoops so that the coiled spring 18 is positioned within the chamber 7 with its ends aligned towards the top and bottom surfaces 4, 5 of the cage 1. In yet additional variations, the springs may be replaced by coils positioned in the chambers 7.

In additional variations of the first embodiment of the invention, the top and bottom surfaces 4, 5 of the cage 1 may be configured with a convex mesh structure serving as flexible structure casting the uneven surfaces of the end-plates of the upper and lower vertebrae V1, V2 and presenting a modulated flexibility depending on the size of the meshes and the thickness of the links.

In a second embodiment of the invention, flexible strands 17.2 may also be arranged on the top and bottom surfaces 4.2b, 5.2b of an expandable cage 1.2, such as expandable cages described in WO2022/061477 and WO2022/23957. FIGS. 20 and 21 represent an expandable cage 1.2, where flexible strands 17.2 are mounted within buffer slits 16 on the top and bottom surfaces 4.2b, 5.2b of an extension member 21, which is stowed within a hosting structure 20 having its own top and bottom surfaces 4.2a, 5.2a. The cage 1.2 of this second embodiment is inserted between the upper and lower vertebrae V1, V2 in the position shown in FIG. 20, with its lateral surfaces 6.2a, 6.2b first engaging the endplates of the vertebrae V1, V2, and then, once positioned at its final location for delivery, being rotated 90° for deployment of its extension member 21, as shown in FIG. 21. The additional benefit of the invention in this second embodiment is that when the extension member 21 is stowed for insertion in the interbody space, the flexible strands 17.2 protrude laterally, instead of protruding beyond the surfaces of the cage 1.2 which engage the vertebrae V1, V2 during the insertion of the cage. The flexible strands 17.2 mounted on the extension member 21 are thus shielded within the hosting structure 20 during the insertion and delivery of the cage 1.2 and the impactation of the cage 1.2 between two vertebrae V1, V2 cannot break the flexible strands 17.2 or otherwise alter their structure during the delivery of the cage 1.2.

As shown in FIG. 21, after the insertion of the cage 1.2 and the deployment of 90° of the extension member 21 according to the inventions in WO2022/061477 and WO2022/23957, the top and bottom surfaces 4.2b, 5.2b of the extension member 21 with their flexible strands 17.2 gain their upward/downward orientation for resting against upper and lower vertebrae V1, V2, applying their flexible characteristics according to the invention of this second embodiment. In a variation of this second embodiment, flexible strands 17.2 may additionally be arranged on the top and bottom surfaces 4.2a, 5.2a of the hosting member 20.

Figure 22:
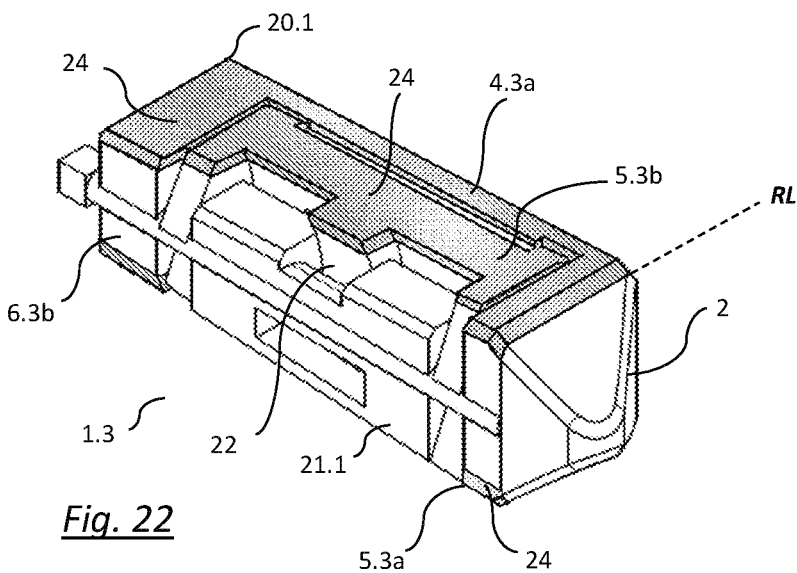
FIG. 22 represents a perspective front view of the expandable cage of the third embodiment with layers of flexible material, in stowed configuration.
Figure 23:
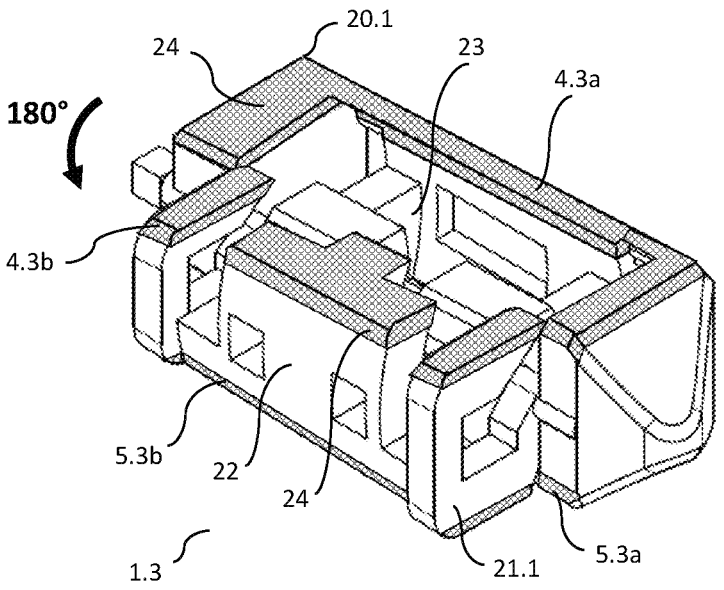
FIG. 23 represents a perspective front view of the same expandable cage as in FIG. 22, in deployed configuration.

FIGS. 22 and 23 describe a third embodiment of the invention, where the expandable cage 1.3 comprises a hosting structure 20.1 and a stowable extension member 21.1 which includes a curved plug structure 22 which has its long dimension aligned with the longitudinal axis of the hosting structure 20.1 and is configured to deploy from within an open curved hosting chamber 23 arranged in the hosting structure 20.1. The purpose of the curved plug structure 22 is to maximize the mass of material in the extension member 21.1 and in the hosting member 20.1, with compatible arcs of the curvature of the curved hosting chamber 23 and of the curvature of the curved plug structure 22 to avoid any cam effect of the extension member 21.1 when it is deployed from its stowed configuration according to the invention in WO2022/061477. The maximization of material mass can be beneficial for promoting intervertebral fusion where the material has osseo-integration properties, such as when it is made with lattice or coiled strands structures. Both the hosting structure 20.1 and the extension member 21.1 may have layers 24 on their top and bottom surfaces 4.3a, 4.3b, 5.3a, 5.3b made of thin lattice structures or of thinly coiled strands to provide degrees of elasticity to those layers which are superior to the elasticity of the remainder of the structures of the cage 1.3 below the layers 24. The limits of these less elastic structures or entirely rigid structures define the rigid levels "RL" and serve as the restraining means within the scope of the invention.

A fourth embodiment of the invention is represented in FIGS. 24 to 27, of an expandable cage 1.4 having, in its stowed configuration, an essentially cylindric cross-section, as described in certain embodiments of WO 2022/232957. The cage 1.4 has one hosting structure 20.3 and one extension member 21.3 configured with several blocks 25 made in open-pore material, such as lattice or coiled strands structures, connected by rigid members 26a, 26b. The blocks 25 have lateral walls 27 coated with homogenous coatings 28, which stop relatively short of the respective top and bottom surfaces 4.4a, 4.4b, 5.4a, 5.4b of the hosting structure 20.2 and extension member 21.2. The layers 24.1 so arranged, represent a flexible structure on the extremities of the respective top and bottom surfaces 4.4a, 4.4b, 5.4a, 5.4b of the blocks 25. The rigid or restraining frame in this third embodiment defining the rigid levels "RL" is provided by the surface of the coatings 28 arranged on the lateral walls 27 of the blocks 25. The other advantage of the coatings 28 is to provide smooth surfaces to reduce the friction between the coated lateral walls 27 of the respective blocks 25 of the hosting structure 20.2 and of the extension member 21.2, during the deployment process of the extension member 21.2 into the configuration shown in FIG. 25.

Figures 24, 25, 26, 27:
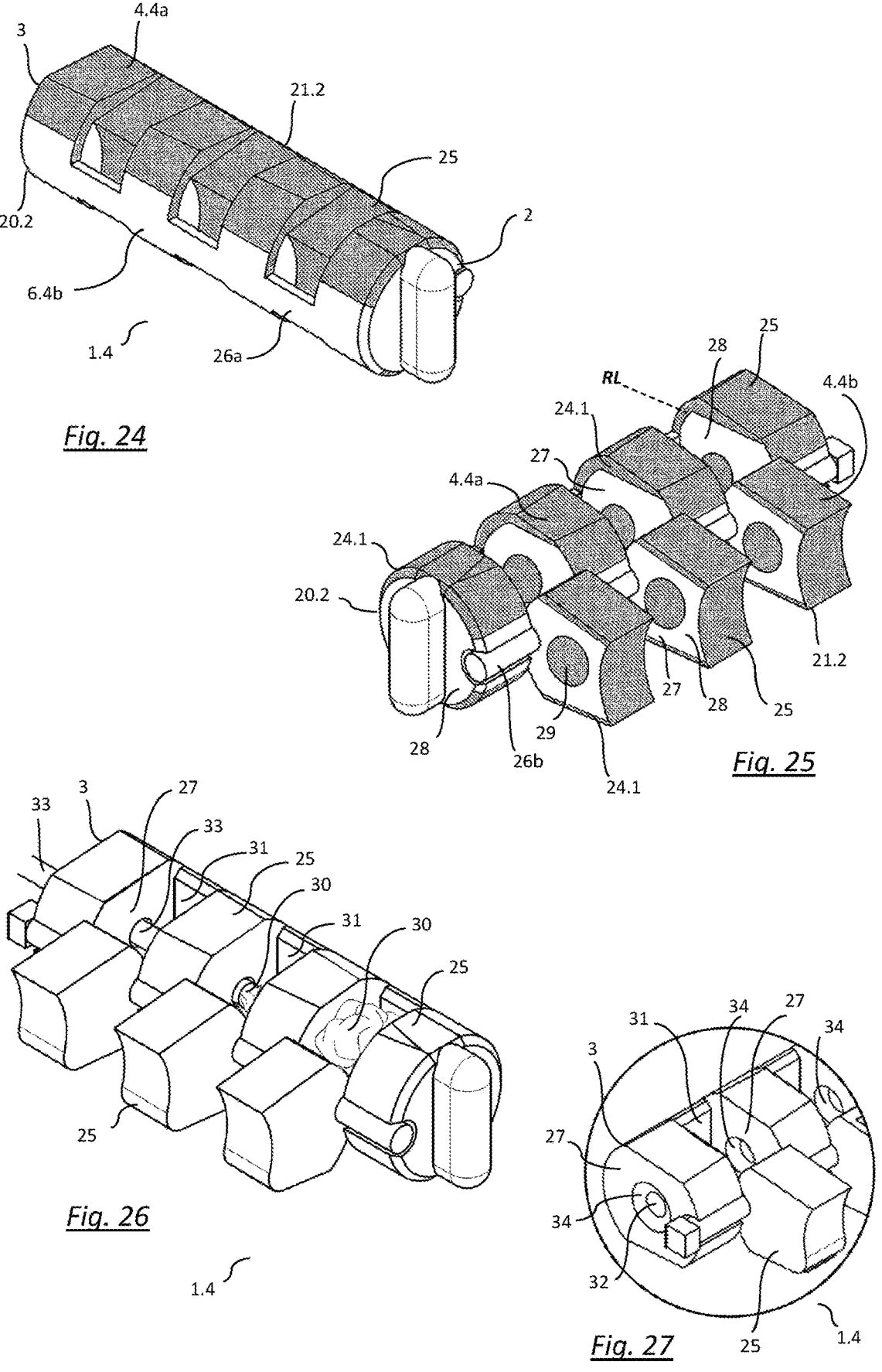
FIG. 24 represents a perspective front view of the expandable cage of the fourth embodiment with homogenous coatings, in stowed configuration.
FIG. 25 represents a perspective front view of the same expandable cage as in FIG. 24, in deployed configuration.
FIG. 26 represents a perspective front view of the expandable cage of the fourth embodiment in deployed configuration with a graft material delivery tube.
FIG. 27 represents a close-up perspective rear view of the rear of the expandable cage of the fourth embodiment in deployed configuration with funneled apertures.

According to FIG. 25, the flexibility of the layers 24.1 on the blocks 25 may be modulated by different perimeters of the surface of the lateral walls 27 of the blocks 25 being covered by the coatings 28: the gradient arranged on the coatings 28 on the blocks 25 of the hosting structure 20.2 shown in FIG. 25 will gradually increase the flexibility of the cage 1.4 on the top and bottom surfaces 4.4a, 4.5b of the hosting structure 20.2, where the layers 24.1 gradually become thicker. The surfaces of the coatings 28 may have any desired pattern and represent any shape. The coatings 28 may also be applied only on one of the lateral walls 27 of the blocks 25, for instance to introduce a directional flexibility to the blocks 25 or, on the contrary on other additional surfaces of the blocks 25 to increase the rigidity. In other variations of this fourth embodiment, the coatings 28 may also have openings 29 to allow bone growth to spread into the blocks 25, or even wide openings across the entire width of the lateral walls 27 of the blocks 25 to introduce one or more flexible layers 24.1 also on other portions of the blocks 25, elsewhere than on its top and bottom surfaces 4.4a, 4.4b, 5.4a, 5.4b.

In order to deliver graft material 30 into the interstices 31 between the blocks 25 of the cage 1.4 after the deployment of the extension member 21.2, openings 32 may be arranged in the lateral walls 27 of the blocks 25 to provide passage to a tube 33. As described in FIG. 26, the tube 33 is introduced via the rear part 3 of the cage 1.4 across the openings 32 across the blocks 25 to deliver the graft material 30 through the tube 33, successively into each of the interstices 31 between the blocks 25. FIG. 27 represents funneled 34 openings 32 to ease the introduction of the tube 33 across the successive openings 32 in the blocks 25.

The instrument to insert, deliver and deploy the expandable cages of the second to fourth embodiments is described in FIGS. 28 and 30 to 33. The instrument 35 comprises a handle 36, three rods 37, 38*a*, 38*b*, which are held together by the handle 36 and by a connector member 39. The median rod 37 is solidarized with the handle 36 and with the connector member 39 and is configured to be attached, at its distal end, to the bore 40 arranged in the rear part 3.3 of the cage 1.3 represented in FIG. 29. The function of this median rod 37 is to push the cage 1.3 between two vertebrae and to induce its pivoting, by the corresponding rotation of the handle 36. One mobile rod 38*a* is positioned adjacent to the median rod 37 and has a distal end configured to engage the rear end of the shaft 41 of the extension member 21.1 of the expandable cage 1.3, in order to rotate the shaft 41 and pivot the extension member 21.1 outwards, away from the hosting structure 20.1 of the expandable cage 1.3.

Figure 30:
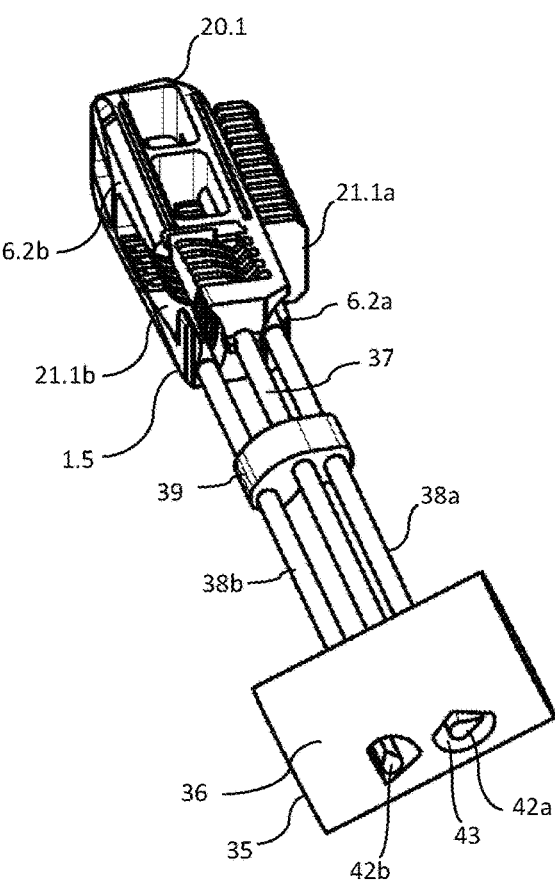
FIG. 30 represents a perspective view of the instrument mounted on an expandable cage with two extension members.

A second mobile rod 38*b* is mounted on the other side of the median rod 37 and is configured to engage a second extension member 21.1*b* such as the one configured in the expandable cage 1.5 shown in FIG. 30, which is configured with two extension members 21.1*a*, 21.1*b*. The function of the mobile rods 38*a* and 38*b* is to induce the pivoting of the extension members 21.1*a*, 21.1*b* and their deployment outwards away from the lateral sides 6.2*a*, 6.2*b* of the expandable cage 1.5. The mobile rods 38*a* and 38*b* are not solidarized with the connector member 39, nor with the handle 36, so as to allow a revolution of said mobile rods 38*a* and 38*b* in their respective conduits through the connector member 39 and through the handle 36 to induce the pivoting of the extension members 21.1*a*, 21.1*b* of the expandable cage 1.5.

Figure 28:
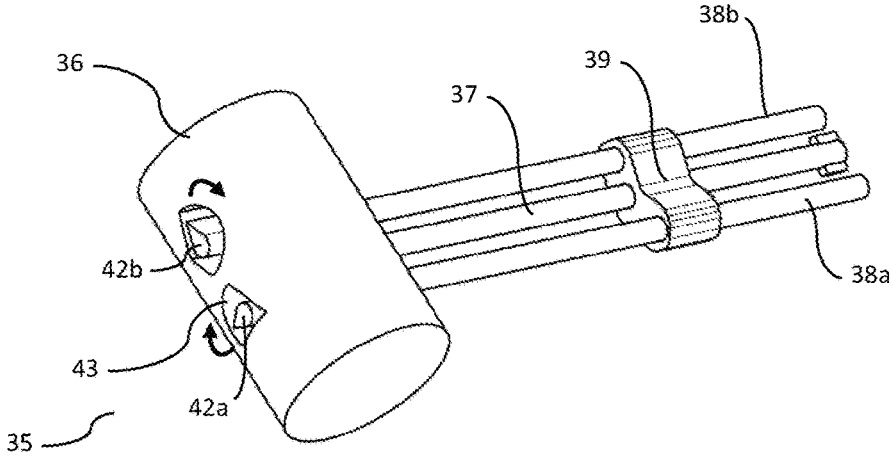
FIG. 28 represents a perspective view of the instrument for the delivery of the cage of the second to fourth embodiments of the invention.
Figure 29:
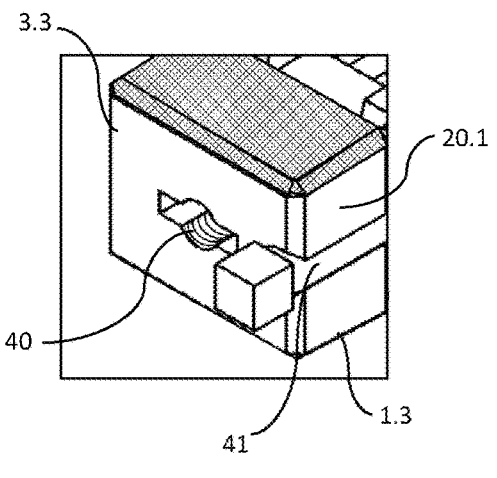
FIG. 29 represents a close-up perspective rear view of the rear of the expandable cage of the third embodiment.

FIGS. 28 and 30 show two triggers 42*a*, 42*b*, mounted at the proximal ends of the mobile rods 38*a* and 38*b*, respectively, and which are nested within housings 43 arranged in the handle 36. Actuation of the triggers 42*a*, 42*b* in either direction causes the extension members 21.1*a*, 21.1*b* of the cage 1.5 to deploy from or to stow within the hosting structure 20.1. Both triggers 42*a*, 42*b* can also be connected by a linking member, for example in order to induce the simultaneous pivoting of the two extension members 21.1*a*, 21.1*b* in the same direction as shown in FIG. 28 or in opposite directions. In variations of the instrument 35, the triggers 42*a*, 42*b* may be replaced by handles.

According to the variation of the instrument 35.1 shown in FIG. 31, the mobile rods 38.1*a*, 38.1*b* mounted on the instrument 35.1, are configured with joints 44*a*, 44*b*, 44*c*, 44*d* enabling the engagement by such mobile rods 38.1*a*, 38.1*b* of two extension members 21.1*a*, 21.1*b* being configured in the cage 1.5 along a variety of different axes and separation distances from each other and from the median rod 37. These joints 44*a*, 44*b*, 44*c*, 44*d* thus allow the use of the same instrument 35.1 for the delivery of different sizes of expandable cages 1.5 with the rear ends of the shafts 41 of its two extension members 21.1*a*, 21.1*b* positioned at different distances from each other and on different planes. As shown in FIG. 32, in this variation, the connection of the rods 37, 38.1*a*, 38.1*b* is achieved by two sets of modular connectors 39.1*a*, 39.1*b* which are configured with an adjustable linking plate 45 connecting two sleeves 46 mounted on the median rod 37 and on the mobile rods 38.1*a*, 38.1*b*, respectively, to enable the stabilization of the instrument 35.1, with rods 37, 38.1*a*, 38.1*b* arranged in different axes and planes to engage the rear ends of the shafts 41 of two extension members 21.1*a*, 21.1*b* of the expandable cage 1.3, 1.5. The relative positions and axes of the rods 37, 38.1*a*, 38.1*b* and their relative separation distances may be frozen by bolts 47 mounted on the linking plates 45 and/or the sleeves 46.

A second variation of the instrument 35.2 is represented in FIG. 33, with one set of joints 44*a*, 44*e* positioned on one side of the modular connectors 39.2*a*, 39.2*b* and a second set of joints 44*b*, 44*c* arranged on the rods 37, 38.1*a*, 38.1*b* on the other side of the modular connectors 39.2*a*, 39.2*b*.

In additional variation of the instrument 35, the median rod 37 can be replaced by a hollow longitudinal structure inside of which the mobile rods 38*a*, 38*b* are configured, this hollow longitudinal structure being fixed to the posterior part of the expandable cage 1.3, 1.5 by any other fastening means. Similarly, any system for engaging the rear end of the shafts 41 of the extension member 21 of the expandable cage 1.3, 1.5 may be envisaged, as well as any other means to connect the rods 37, 38*a*, 39*b* for a stable instrument. Finally, the mobile rods 38*a*, 38*b* may be pivoted by any technical means other than the triggers 42*a*, 42*b*, for example by a system of gears and/or racks and pinions arranged on the rods 37, 38*a*, 38*b* or the joints 44, and actuated by a handle 36 operated in a fixed plane.

It goes without saying that each of the characteristics of each embodiment of the cage 1, 1.1, 1.2, 1.3, 1.4, 1.5 and any of their variations may be applied to any other embodiment or any of their variations.

The embodiments of the invention may apply to any implants separating and/or fusing vertebrae, whether interbody implants, vertebral body replacement implants, interspinous implants and artificial discs. The invention may also apply to the reduction and/or fusion of other bones, such as the hips, the pelvis, and any long bones and joints.

The embodiments of the invention may apply to human spinal columns and to animal spinal columns.

What is claimed is:

1. A dynamically morphing prismatic structure for use in an intervertebral bone fusion implantable device, the structure comprising:

(a) an interlocking modular configuration with structural parts extending between a distal end and a proximal end of the device, the interlocking modular configuration comprising:

at least one stowed structural element operatively interconnected with the interlocking modular configuration, the stowed structural element comprising:

(i) at least one block having an uneven structural geometry adapted to promote osseointegration of the device wherein at least one inner, outer, or side wall of the at least one block is coated or sprayed with a friction-reducing coating adapted to permit frictionless movement between the block and adjacent structures of the interlocking modular configuration; and (ii) wherein the stowed structural element being operable to transition between:

a stowed compact position for insertion between an upper vertebra and a lower vertebra; and an unstowed expanded position causing an increase in both surface area and volume with the device reconfiguring spatially, (b) an engagement element positioned at the distal end of the device;

(c) a removable instrument operatively coupled to the proximal end of the interlocking modular configuration, the removable instrument being adapted to advance the engagement element, wherein the engagement element facilitates:

(i) increasing an interstitial space between the upper vertebra and the lower vertebra; and (ii) delivering the device in a compact first form factor defined by a first surface area; and a first volume within the interstitial space;

(d) wherein:

(i) structural parts of the interlocking modular configuration being positioned adjacent to the at least one block of the stowed structural element, such that the friction-reducing coating is applied on one or more of an inner, outer, or side wall of a block adjacent to structural elements of the interlocking modular configuration in the compact first form factor; and (ii) the spatial reconfiguration of the device by operation of the removable instrument, causing the interlocking modular configuration and the stowed structural element to transition from the compact first form factor to one of increased or expanded second form factor, wherein:

(A) the second form factor is characterized by an increased second volume and increased second surface area relative to the first form factor; and (B) the transition is facilitated by reduced sliding friction during displacement of the at least one block of the stowed structural element relative to the structural parts of the interlocking modular configuration.

2. The intervertebral bone fusion implantable device of claim 1, wherein the at least one block of the structural element is fabricated from a material selected from the group consisting of an open-pore, coiled strands, denser, thin and thicker lattice, and equivalent material and the friction reducing coating being applied to minimize shear forces and increase durability during displacement or rotation while promoting ease of relative motion between the block and adjacent structures.

3. The intervertebral bone fusion implantable device of claim 1, wherein the displacement of one block relative to an adjacent structure is planar.

4. The intervertebral bone fusion implantable device of claim 1, wherein the displacement of one block relative to an adjacent structure is rotational.

5. The intervertebral bone fusion implantable device of claim 1, wherein the friction-reducing coating applied to the surface of one or more of the inner, outer, or side walls of the at least one block enables one of ease of assembly and disassembly.

6. The intervertebral bone fusion implantable device of claim 1, wherein the friction-reducing coating is applied to the surface of one or more of the inner, outer, or side walls at the at least one block enables the dynamic spatial reconfiguration of the device.

7. The intervertebral bone fusion implantable device of claim 1, wherein the friction-reducing coating is applied to the surface of one or more of the inner, outer, or side walls at the at least one block and provides structural elasticity to enable dynamic, torsional, rotational stresses due to spinal kinetics and posture.

* * * * *